(12) United States Patent
Walch

(10) Patent No.: US 11,439,097 B1
(45) Date of Patent: Sep. 13, 2022

(54) MAIZE INBRED PH4DAZ

(71) Applicant: PIONEER HI-BRED INTERNATIONAL, INC., Johnston, IA (US)

(72) Inventor: Matthew David Walch, Moorhead, MN (US)

(73) Assignee: PIONEER HI-BRED INTERNATIONAL, INC.

( * ) Notice: Subject to any disclaimer, the term of this patent is extended or adjusted under 35 U.S.C. 154(b) by 87 days.

(21) Appl. No.: 17/067,838

(22) Filed: Oct. 12, 2020

(51) Int. Cl.
*A01H 6/46* (2018.01)
*A01H 5/10* (2018.01)

(52) U.S. Cl.
CPC ............. *A01H 6/4684* (2018.05); *A01H 5/10* (2013.01)

(58) Field of Classification Search
None
See application file for complete search history.

(56) References Cited

U.S. PATENT DOCUMENTS

| | | |
|---|---|---|
| 8,592,666 B1 | 11/2013 | Grote |
| 8,686,256 B1 | 4/2014 | Scott |
| 2007/0180555 A1* | 8/2007 | Uhr ...................... A01H 6/4684 800/278 |

OTHER PUBLICATIONS

U.S. Appl. No. 17/076,978 for Maize Hybrid X95P914, filed Oct. 22, 2020.
U.S. Appl. No. 17/076,974 for Maize Hybrid X85P998, filed Oct. 22, 2020.
U.S. Appl. No. 17/076,972 for Maize Hybrid X80P536, filed Oct. 22, 2020.

* cited by examiner

Primary Examiner — Vinod Kumar

(57) ABSTRACT

A novel maize variety designated PH4DAZ and seed, plants and plant parts thereof are provided. Methods for producing a maize plant comprise crossing maize variety PH4DAZ with another maize plant are provided. Methods for producing a maize plant containing in its genetic material one or more traits introgressed into PH4DAZ through backcross conversion and/or transformation, and to the maize seed, plant and plant part produced thereby are provided. Hybrid maize seed, plants or plant parts are produced by crossing the variety PH4DAZ or a locus conversion of PH4DAZ with another maize variety.

20 Claims, No Drawings

MAIZE INBRED PH4DAZ

BACKGROUND

There are numerous steps in the development of any novel, desirable maize variety. Plant breeding begins with the analysis and definition of problems and weaknesses of the current germplasm, the establishment of program goals, and the definition of specific breeding objectives. The next step is selection of germplasm that possess the traits to meet the program goals. The breeder's goal is to combine in a single variety or hybrid, various desirable traits. For field crops, these traits may include resistance to diseases and insects, resistance to heat and drought, reducing the time to crop maturity, greater yield, altered fatty acid profile, abiotic stress tolerance, improvements in compositional traits, and better agronomic characteristics and quality.

These product development processes, which lead to the final step of marketing and distribution, can take from six to twelve years from the time the first cross is made until the finished seed is delivered to the farmer for planting. Therefore, development of new varieties and hybrids is a time-consuming process. A continuing goal of maize breeders is to develop stable, high yielding maize varieties and hybrids that are agronomically sound with maximal yield over one or more different conditions and environments.

SUMMARY

Provided is a novel maize, *Zea mays* L., variety, designated PH4DAZ and processes for making PH4DAZ. Seed of maize variety PH4DAZ, plants of maize variety PH4DAZ, plant parts and cells of maize variety PH4DAZ, and to processes for making a maize plant that comprise crossing maize variety PH4DAZ with another maize plant are provided. Also provided are maize plants having all the physiological and morphological characteristics of the inbred maize variety PH4DAZ.

Processes are provided for making a maize plant containing in its genetic material one or more traits introgressed into PH4DAZ through one or more of backcross conversion, genetic manipulation and transformation, and to the maize seed, plant and plant parts produced thereby. Hybrid maize seed, plants or plant parts produced by crossing the variety PH4DAZ or a locus conversion of PH4DAZ with another maize variety are also provided.

The inbred maize plant may further comprise a cytoplasmic or nuclear factor capable of conferring male sterility or otherwise preventing self-pollination, such as by self-incompatibility. Parts of the maize plant described herein are also provided, for example, pollen obtained from an inbred plant and an ovule of the inbred plant.

Seed of the inbred maize variety PH4DAZ is provided. The inbred maize seed may be an essentially homogeneous population of inbred maize seed of the variety designated PH4DAZ. Essentially homogeneous populations of inbred seed are generally free from substantial numbers of other seed. Therefore, inbred seed generally forms at least about 97% of the total seed. The population of inbred maize seed may be particularly defined as being essentially free from hybrid seed. The inbred seed population may be separately grown to provide an essentially homogeneous population of inbred maize plants designated PH4DAZ.

Compositions are provided comprising a seed of maize variety PH4DAZ comprised in plant seed growth media. In certain embodiments, the plant seed growth media is a soil or synthetic cultivation medium. In specific embodiments, the growth medium may be comprised in a container or may, for example, be soil in a field.

Maize variety PH4DAZ comprising an added heritable trait is provided. The heritable trait may comprise a genetic locus that is a dominant or recessive allele. In certain embodiments, a plant of maize variety PH4DAZ comprising a single locus conversion is provided. The locus conversion may be one which confers one or more traits such as, for example, male sterility, herbicide tolerance, insect resistance, disease resistance (including, for example) bacterial, fungal, nematode or viral disease, waxy starch, modified fatty acid metabolism, modified phytic acid metabolism, modified carbohydrate metabolism and modified protein metabolism is provided. The trait may be, for example, conferred by a naturally occurring maize gene introduced into the genome of the variety by backcrossing, a natural or induced mutation, or a transgene introduced through genetic transformation techniques. When introduced through transformation, a genetic locus may comprise one or more transgenes integrated at a single chromosomal location.

An inbred maize plant of the variety designated PH4DAZ is provided, wherein a cytoplasmically-inherited trait has been introduced into the inbred plant. Such cytoplasmically-inherited traits are passed to progeny through the female parent in a particular cross. An exemplary cytoplasmically-inherited trait is the male sterility trait. Cytoplasmic-male sterility (CMS) is a pollen abortion phenomenon determined by the interaction between the genes in the cytoplasm and the nucleus. Alteration in the mitochondrial genome and the lack of restorer genes in the nucleus will lead to pollen abortion. With either a normal cytoplasm or the presence of restorer gene(s) in the nucleus, the plant will produce pollen normally. A CMS plant can be pollinated by a maintainer version of the same variety, which has a normal cytoplasm but lacks the restorer gene(s) in the nucleus, and continues to be male sterile in the next generation. The male fertility of a CMS plant can be restored by a restorer version of the same variety, which has the restorer gene(s) in the nucleus. With the restorer gene(s) in the nucleus, the offspring of the male-sterile plant can produce normal pollen grains and propagate. A cytoplasmically inherited trait may be a naturally occurring maize trait or a trait introduced through genetic transformation techniques.

A tissue culture of regenerable cells of a plant of variety PH4DAZ is provided. The tissue culture can be capable of regenerating plants capable of expressing all of the physiological and morphological or phenotypic characteristics of the variety, and of regenerating plants having substantially the same genotype as other plants of the variety. Examples of some of the physiological and morphological characteristics that may be assessed include characteristics related to yield, maturity, and kernel quality. The regenerable cells in such tissue cultures can be derived, for example, from embryos, meristematic cells, immature tassels, microspores, pollen, leaves, anthers, roots, root tips, silk, flowers, kernels, ears, cobs, husks, or stalks, or from callus or protoplasts derived from those tissues. Maize plants regenerated from the tissue cultures, and plants having all the physiological and morphological characteristics of variety PH4DAZ are also provided.

Processes are provided for producing maize seeds or plants, which processes generally comprise crossing a first parent maize plant as a male or female parent with a second parent maize plant, wherein at least one of the first or second parent maize plants is a plant of the variety designated PH4DAZ. These processes may be further exemplified as processes for preparing hybrid maize seed or plants, wherein a first inbred maize plant is crossed with a second maize plant of a different, distinct variety to provide a hybrid that has, as one of its parents, the inbred maize plant variety PH4DAZ. In these processes, crossing will result in the production of seed. The seed production occurs regardless of whether the seed is collected or not.

In some embodiments, the first step in "crossing" comprises planting, such as in pollinating proximity, seeds of a first and second parent maize plant, and preferably, seeds of a first inbred maize plant and a second, distinct inbred maize plant. Where the plants are not in pollinating proximity, pollination can be achieved by transferring a pollen or tassel bag from one plant to the other as described below.

A second step comprises cultivating or growing the seeds of said first and second parent maize plants into plants that bear flowers—male flowers (tassels) and female flowers (silks).

A third step comprises preventing self-pollination of the plants, i.e., preventing the silks of a plant from being fertilized by any plant of the same variety, including the same plant. This can be done by emasculating the male flowers of the first or second parent maize plant, (i.e., treating or manipulating the tassels so as to prevent pollen production, to produce an emasculated parent maize plant). Self-incompatibility systems may also be used in some hybrid crops for the same purpose. Self-incompatible plants still shed viable pollen and can pollinate plants of other varieties but are incapable of pollinating themselves or other plants of the same variety.

A fourth step may comprise allowing cross-pollination to occur between the first and second parent maize plants. When the plants are not in pollinating proximity, this is done by placing a bag, usually paper or glassine, over the tassels of the first plant and another bag over the silks of the incipient ear on the second plant. The bags are left in place for at least 24 hours. Since pollen is viable for less than 24 hours, this assures that the silks are not pollinated from other pollen sources, that any stray pollen on the tassels of the first plant is dead, and that the only pollen transferred comes from the first plant. The pollen bag over the tassel of the first plant is then shaken vigorously to enhance release of pollen from the tassels, and the shoot bag is removed from the silks of the incipient ear on the second plant. Finally, the pollen bag is removed from the tassel of the first plant and is placed over the silks of the incipient ear of the second plant, shaken again and left in place. Yet another step comprises harvesting the seeds from at least one of the parent maize plants. The harvested seed can be grown to produce a maize plant or hybrid maize plant.

Also provided are maize seed and plants produced by a process that comprises crossing a first parent maize plant with a second parent maize plant, wherein at least one of the first or second parent maize plants is a plant of the variety designated PH4DAZ. In one embodiment, maize seed and plants produced by the process are first generation (F1) hybrid maize seed and plants produced by crossing an inbred with another, distinct plant such as another inbred. Seed of an F1 hybrid maize plant and an F1 hybrid maize plant and seed thereof are provided.

The genetic complement of the maize plant variety designated PH4DAZ is provided. The phrase "genetic complement" is used to refer to the aggregate of nucleotide sequences, the expression of which sequences defines the phenotype of, in the present case, a maize plant, or a cell or tissue of that plant. A genetic complement thus represents the genetic make-up of an inbred cell, tissue or plant, and a hybrid genetic complement represents the genetic make-up of a hybrid cell, tissue or plant. Maize plant cells that have a genetic complement in accordance with the inbred maize plant cells disclosed herein, and plants, seeds and diploid plants containing such cells are provided.

Plant genetic complements may be assessed by genetic marker profiles, and by the expression of phenotypic traits that are characteristic of the expression of the genetic complement, e.g., isozyme typing profiles. It is understood that variety PH4DAZ could be identified by any of the many well-known techniques used for genetic profiling disclosed herein.

In another aspect, hybrid genetic complements are provided, as represented by maize plant cells, tissues, plants, and seeds, formed by the combination of a haploid genetic complement of an inbred maize plant disclosed herein with a haploid genetic complement of a second maize plant, such as, another, distinct inbred maize plant. In another aspect, a maize plant regenerated from a tissue culture that comprises a hybrid genetic complement of the inbred maize plant disclosed herein.

Methods of producing an inbred maize plant derived from the maize variety PH4DAZ are provided, the method comprising the steps of: (a) preparing a progeny plant derived from maize variety PH4DAZ, wherein said preparing comprises crossing a plant of the maize variety PH4DAZ with a second maize plant; (b) crossing the progeny plant with itself or a second plant to produce a seed of a progeny plant of a subsequent generation; (c) repeating steps (a) and (b) with sufficient inbreeding until a seed of an inbred maize plant derived from the variety PH4DAZ is produced. In the method, it may be desirable to select particular plants resulting from step (c) for continued crossing according to steps (b) and (c). By selecting plants having one or more desirable traits, an inbred maize plant derived from the maize variety PH4DAZ is obtained which possesses some of the desirable traits of maize variety PH4DAZ as well as potentially other selected traits.

DETAILED DESCRIPTION

A new and distinctive maize inbred variety designated PH4DAZ, which has been the result of years of careful breeding and selection in a comprehensive maize breeding program is provided.

Definitions

Maize (*Zea mays*) can be referred to as maize or corn. Certain definitions used in the specification are provided below. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted.

ABIOTIC STRESS TOLERANCE: resistance to non-biological sources of stress conferred by traits such as nitrogen utilization efficiency, altered nitrogen responsiveness, drought resistance, cold, and salt resistance ABTSTK=ARTIFICIAL BRITTLE STALK: A count of the number of "snapped" plants per plot following machine snapping. A snapped plant has its stalk completely snapped at a node between the base of the plant and the node above the ear. Expressed as percent of plants that did not snap.

ALLELE: Any of one or more alternative forms of a genetic sequence. In a diploid cell or organism, the two alleles of a given sequence typically occupy corresponding loci on a pair of homologous chromosomes.

ANTHESIS: The time of a flower's opening.

ANTIOXIDANT: A chemical compound or substance that inhibits oxidation, including but not limited to tocopherol or tocotrienols.

ANT ROT=ANTHRACNOSE STALK ROT (*Colletotrichum graminicola*): A 1 to 9 visual rating indicating the resistance to Anthracnose Stalk Rot. A higher score indicates a higher resistance. Data are collected only when sufficient selection pressure exists.

BACKCROSSING: Process in which a breeder crosses a hybrid progeny variety back to one of the parental genotypes one or more times.

BACKCROSS PROGENY: Progeny plants produced by crossing one maize line (recurrent parent) with plants of another maize line (donor) that comprise a desired trait or locus, selecting progeny plants that comprise the desired trait or locus, and crossing them with the recurrent parent one or more times to produce backcross progeny plants that comprise said trait or locus.

BARPLT=BARREN PLANTS: The percent of plants per plot that were not barren (lack ears).

BORBMN=ARTIFICIAL BRITTLE STALK MEAN: The mean percent of plants not "snapped" in a plot following artificial selection pressure. A snapped plant has its stalk completely snapped at a node between the base of the plant and the node above the ear. Expressed as percent of plants that did not snap. A higher number indicates better tolerance to brittle snapping.

BREEDING CROSS: A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed.

CELL: Cell as used herein includes a plant cell, whether isolated, in tissue culture or incorporated in a plant or plant part.

CLDTST=COLD TEST: The percent of plants that germinate under cold test conditions.

CLN=CORN LETHAL NECROSIS: Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance. Data are collected only when sufficient selection pressure exists.

CMSMT=COMMON SMUT: This is the percentage of plants not infected with Common Smut. Data are collected only when sufficient selection pressure exists.

COMRST=COMMON RUST (*Puccinia sorghi*): A 1 to 9 visual rating indicating the resistance to Common Rust. A higher score indicates a higher resistance. Data are collected only when sufficient selection pressure exists.

CROSS POLLINATION: Fertilization by the union of two gametes from different plants.

CROSSING: The combination of genetic material by traditional methods such as a breeding cross or backcross, but also including protoplast fusion and other molecular biology methods of combining genetic material from two sources.

D/D=DRYDOWN: This represents the relative rate at which a hybrid will reach acceptable harvest moisture compared to other hybrids on a 1 to 9 rating scale. A high score indicates a hybrid that dries relatively fast while a low score indicates a hybrid that dries slowly.

DIPERS=*DIPLODIA* EAR MOLD SCORES (*Diplodia maydis* and *Diplodia macrospora*): A 1 to 9 visual rating indicating the resistance to *Diplodia* Ear Mold. A higher score indicates a higher resistance. Data are collected only when sufficient selection pressure exists.

DIPLOID PLANT PART: Refers to a plant part or cell that has a same diploid genotype.

DIPROT=*DIPLODIA* STALK ROT SCORE: Score of stalk rot severity due to *Diplodia* (*Diplodia maydis*). Expressed as a 1 to 9 score with 9 being highly resistant. Data are collected only when sufficient selection pressure exists.

D/T=DROUGHT TOLERANCE: This represents a 1 to 9 rating for drought tolerance, and is based on data obtained under stress conditions. A high score indicates good drought tolerance and a low score indicates poor drought tolerance. Data are collected only when sufficient selection pressure exists.

EARMLD=GENERAL EAR MOLD: Visual rating (1 to 9 score) where a 1 is very susceptible and a 9 is very resistant. This is based on overall rating for ear mold of mature ears without determining the specific mold organism, and may not be predictive for a specific ear mold. Data are collected only when sufficient selection pressure exists.

EARHT=EDEARHT=EAR HEIGHT: The ear height is a measure from the ground to the highest placed developed ear node attachment and is measured in inches (EARHT) or cm (EDEARHT).

EARSZ=EAR SIZE: A 1 to 9 visual rating of ear size. The higher the rating the larger the ear size.

EDANTCOLs=ANTHER COLOR: Rated on a 1 to 7 scale where 1 is green, 2 is yellow, 3 is pink, 5 is red, and 7 is purple.

EDantants=ANTHER ANTHOCYANIN COLOR INTENSITY: A measure of anther anthocyanin color intensity rated on a 1 to 9 scale where 1 is absent or very weak, 3 is weak, 5 is medium, 7 is strong, and 9 is very strong. Observed in the middle third of the main branch on fresh anthers.

EDbarants=GLUME ANTHOCYANIN COLORATION AT BASE (WHOLE PLANT, EAR INSERTION LEVEL): A measure of the color intensity at the base of the glume, rated on a 1 to 9 scale where 1 is absent or very weak, 3 is weak, 5 is medium, 7 is strong, and 9 is very strong. Observed in the middle third of the main branch of the tassel.

EDBARCOLs=BAR GLUME COLOR INTENSITY: A measure of the bar glume color intensity. Bar glume is a dark purple band that may occur on the bottom of a glume. Bar glume color intensity is measured on a scale of 1 to 7 where 1 is absent, 2 is weak, 3 is medium, 5 is strong, and 7 is very strong.

EDBRROANTs=BRACE ROOTS ANTHOCYANIN COLORATION: A measure of the color intensity of the brace roots rated on a 1 to 9 scale where 1 is absent or very weak, 3 is weak, 5 is medium, 7 is strong, and 9 is very strong. Observed when well developed and fresh brace roots are present on 50% of plants.

EDCOBAINTs=COB GLUME ANTHOCYANIN COLOR INTENSITY: Rated on a 1 to 9 scale where 1 is absent or very weak, 3 is weak, 5 is medium, 7 is strong, and 9 is very strong. Anthocyanin coloration should be observed on the middle third of the uppermost cob, after the removal of some of the grains.

EDCOBCOLs=COB COLOR: A measure of the intensity of pink or salmon coloration of the cob, rated on a 1 to 9 scale where 1 is absent or white, 2 is light pink, 3 is pink, 4 is medium red, 5 is red, 6 is medium red, 7 is dark red, 8 is dark to very dark red, and 9 is present.

EDCOBDIA=COB DIAMETER: Measured in mm.

EDCOBICAs=COB ANTHOCYANIN COLOR INTENSITY: A measure of the intensity of pink or salmon coloration of the cob, rated on a 1 to 9 scale where 1 is very weak, 3 is weak, 5 is medium, 7 is strong, and 9 is very strong.

EDEARDIA=EAR DIAMETER: Measured in mm.

EDEARHULs=EAR HUSK LENGTH: A measure of ear husk length rated on a 1 to 9 scale where 1 is very short, 3 is short, 5 is medium, 7 is long, and 9 is very long.

EDEARLNG=EAR LENGTH: Measured in mm.

EDEARROW=NUMBER OF ROWS OF GRAIN ON EAR.

EDEARSHAs=EAR SHAPE (TAPER): Rated on a 1 to 3 scale where 1 is conical, 2 is conico-cylindrical, and 3 is cylindrical.

EDEARSHLs=EAR SHANK LENGTH SCALE: A measure of the length of the ear shank or peduncle, rated on a 1 to 9 scale where 1 is very short, 3 is short, 5 is medium, 7 is long, 9 is very long.

EDFILEANs=SHEATH ANTHOCYANIN COLOR INTENSITY AT FIRST LEAF STAGE: A measure of the anthocyanin color intensity of the sheath of the first leaf, rated on a 1 to 9 scale where 1 is absent or very weak, 3 is weak, 5 is medium, 7 is strong, and 9 is very strong.

EDFILECOs=FOLIAGE INTENSITY OF GREEN COLOR: A measure of the green coloration intensity in the leaves, rated on a 1 to 3 scale where 1 is light, 2 is medium, and 3 is dark.

EDFILESHs=LEAF TIP SHAPE: An indication of the shape of the apex of the first leaf, rated on a 1 to 5 scale where 1 is pointed, 2 is pointed to rounded, 3 is rounded, 4 is rounded to spatulate, and 5 is spatulate.

EDGLUANTs=GLUME ANTHOCYANIN COLOR EXCLUDING BASE: A measure of the color intensity of the glume excluding the base, rated on a 1 to 9 scale where 1 is absent or very weak, 3 is weak, 5 is medium, 7 is strong, and 9 is very strong. Observed in the middle third of the main branch of the tassel.

EDGLUCOLs=GLUME COLOR: Rated on a 1 to 7 scale where 1 is green, 2 is yellow, 3 is pink, 5 is red, and 7 is purple.

EDKERDOCs=DORSAL SIDE OF GRAIN COLOR: Rated on a 1 to 10 scale where 1 is white, 2 is yellowish white, 3 is yellow, 4 is yellow orange, 5 is orange, 6 is red orange, 7 is red, 8 is purple, 9 is brownish, and 10 is blue black. Observed in the middle third of the uppermost ear when well developed.

EDKERSHAs=KERNEL SHAPE: Rated on a 1 to 3 scale where 1 is round, 2 is kidney-shaped, and 3 is cuneiform.

EDKERTCOs=TOP OF GRAIN COLOR: Rated on a 1 to 10 scale where 1 is white, 2 is yellowish white, 3 is yellow, 4 is yellow orange, 5 is orange, 6 is red orange, 7 is red, 8 is purple, 9 is brownish, and 10 is blue black. Observed in the middle third of the uppermost ear when well developed.

EDLEAANGs=LEAF ANGLE BETWEEN BLADE AND STEM: A measure of the angle formed between stem and leaf, rated on a 1 to 9 scale where 1 is very small (<5 degrees), 3 is small (6 to 37 degrees), 5 is medium (38 to 62 degrees), 7 is large (63 to 90 degrees), and 9 is very large (>90 degrees). Observed on the leaf just above the upper ear.

EDLEAATTs=LEAF ATTITUDE OF ENTIRE PLANT: A measure of leaf curvature or attitude, rated on a 1 to 9 scale where 1 is absent or very slightly recurved, 3 is slightly recurved, 5 is moderately recurved, 7 is strongly recurved, and 9 is very strongly recurved. Observed on the leaf just above the upper ear.

EDLEALNGs=LEAF LENGTH SCORE: A measure of leaf length rated on a 1 to 9 scale where 1 indicates <0.70 m, 3 indicates 0.70 m to 0.80 m, 5 indicates 0.80 m to 0.90 m, 7 indicates 0.90 m to 1 m, and 9 indicates >1.00 m.

EDLEAWID=LEAF WIDTH OF BLADE: A measure of the average leaf width in cm.

EDLELIANTs=LEAF LIMB ANTHOCYANIN COLOR INTENSITY OF ENTIRE PLANT: A measure of the leaf limb anthocyanin coloration, rated on a 1 to 9 scale with 1 being absent or very weak, 3 being weak, 5 being medium, 7 being strong, and 9 being very strong.

EDNODANTS=NODES ANTHOCYANIN COLOR INTENSITY: A measure of the anthocyanin coloration of nodes, rated on a 1 to 9 scale where 1 is absent or very weak, 3 is weak, 5 is medium, 7 is strong, and 9 is very strong.

EDRATIOEP=RATIO HEIGHT OF INSERTION OF PEDUNCLE OF UPPER EAR TO PLANT LENGTH.

EDSHEAHAs=LEAF SHEATH HAIRNESS SCALE: Rated on a 1 to 6 scale where 1 indicates none and 6 indicates fuzzy.

EDSHEAANTs=SHEATH ANTHOCYANIN COLOR INTENSITY: Rated on a 1 to 9 scale where 1 is absent or very weak, 3 is weak, 5 is medium, 7 is strong, and 9 is very strong.

EDSLKAINTs=SILK ANTHOCYANIN COLOR INTENSITY: A measure of the color intensity of the silks, rated on a 1 to 9 scale where 1 is absent or very weak, 3 is weak, 5 is medium, 7 is strong, and 9 is very strong.

EDSTLANTs=INTERNODE ANTHOCYANIN COLOR INTENSITY: A measure of anthocyanin coloration of nodes, rated on a 1 to 9 scale where 1 is absent or very weak, 3 is weak, 5 is medium, 7 is strong, and 9 is very strong. Observed just above the insertion point of the peduncle of the upper ear.

EDTA1RYATs=TASSEL LATERAL BRANCH CURVATURE: Rated on a 1 to 9 scale where 1 indicates absent or very slightly recurved (<5 degrees), 3 indicates slightly recurved (6 to 37 degrees), 5 indicates moderately recurved (38 to 62 degrees), 7 indicates strongly recurved (63 to 90 degrees), and 9 indicates very strongly recurved (>90 degrees). Observed on the second branch from the bottom of the tassel.

EDTA1 RYBRs=NUMBER OF PRIMARY LATERAL TASSEL BRANCHES: Rated on a 1 to 9 scale where 1 indicates absent or very few (<4 branches), 3 indicates few (4 to 10), 5 indicates medium (11 to 15), 7 indicates many (16 to 20), and 9 indicates very many (>20).

EDTASAHB=LENGTH OF MAIN AXIS ABOVE HIGHEST LATERAL BRANCH: Length of the tassel's main axis above the highest lateral branch in cm.

EDTASANGs=TASSEL ANGLE BETWEEN MAIN AXIS AND LATERAL BRANCHES: Rated on a 1 to 9 scale where 1 is very small (<5 degrees), 3 is small (6 to 37 degrees), 5 is medium (38 to 62 degrees), 7 is large (63 to 90 degrees), and 9 is very large (>90 degrees). Observed on second branch from bottom of tassel.

EDTASEBRs=SECONDARY TASSEL BRANCHES (NUMBER): The number of secondary tassel branches, rated on a 1 to 7 scale where 1 indicates 0 to 3 branches, 2 indicates 4 to 10, 3 indicates 11 to 15, 5 indicates 16 to 20, and 7 indicates >20.

EDTASLPBRs=PRIMARY TASSEL BRANCH LENGTH: A measure of the length of the primary or lateral tassel branch, rated on a 1 to 9 scale where 1 is very short, 3 is short, 5 is medium, 7 is long, 9 is very long. Observed on the second branch from the bottom of the tassel.

EDTASULB=LENGTH OF MAIN AXIS ABOVE LOWEST LATERAL BRANCH: The length of the tassel's main axis above the lowest lateral branch in cm.

EDZIGZAGs=DEGREE OF STEM ZIG-ZAG: Rated on a scale of 1 to 3 where 1 is absent or very slight, 2 is slight, and 3 is strong.

EGRWTH=EARLY GROWTH: This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute higher score. Data are collected only when sufficient selection pressure exists.

ERTLPN=EARLY ROOT LODGING: An estimate of the percentage of plants that do not root lodge prior to or around anthesis; plants that lean from the vertical axis at an approximately 30° angle or greater would be considered as root lodged. Data are collected only when sufficient selection pressure exists.

ERTLSC=EARLY ROOT LODGING SCORE: Score for severity of plants that lean from a vertical axis at an approximate 30° angle or greater which typically results from strong winds prior to or around flowering recorded within 2 weeks of a wind event. Expressed as a 1 to 9 score with 9 being no lodging. Data are collected only when sufficient selection pressure exists.

ESTCNT=EARLY STAND COUNT: This is a measure of the stand establishment in the spring and represents the number of plants that emerge on per plot basis for the inbred or hybrid.

EYESPT=EYE SPOT (*Kabatiella zeae* or *Aureobasidium zeae*): A 1 to 9 visual rating indicating the resistance to Eye Spot. A higher score indicates a higher resistance. Data are collected only when sufficient selection pressure exists.

F1 PROGENY: A progeny plant produced by crossing a plant of one maize line with a plant of another maize line.

FUSERS=*FUSARIUM* EAR ROT SCORE (*Fusarium moniliforme* or *Fusarium subglutinans*): A 1 to 9 visual rating indicating the resistance to Fusarium Ear Rot. A higher score indicates a higher resistance. Data are collected only when sufficient selection pressure exists.

GDU=GROWING DEGREE UNITS: Using the Barger Heat Unit Theory, which assumes that maize growth occurs in the temperature range 50° F.-86° F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=EDDAYSH=GDU TO SHED: The number of growing degree units (GDUs) or heat units required for an inbred variety or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The units determined by the Barger Method are then divided by 10. The highest maximum temperature used is 86° F. and the lowest minimum temperature used is 50° F. For each inbred or hybrid it takes a certain number of GDUs to reach various stages of plant development.

GDUSLK=EDDAYSLK=GDU TO SILK: The number of growing degree units required for an inbred variety or hybrid to have approximately 50 percent of the plants with silk emergence from time of planting. Growing degree units are calculated by the Barger Method as given in GDUSHD definition and then divided by 10.

GIBERS=*GIBBERELLA* EAR ROT (PINK MOLD) (*Gibberella zeae*): A 1 to 9 visual rating indicating the resistance to *Gibberella* Ear Rot. A higher score indicates a higher resistance. Data are collected only when sufficient selection pressure exists.

GIBROT=*GIBBERELLA* STALK ROT SCORE: Score of stalk rot severity due to *Gibberella* (*Gibberella zeae*). Expressed as a 1 to 9 score with 9 being highly resistant. Data are collected only when sufficient selection pressure exists.

GLFSPT=GRAY LEAF SPOT (*Cercospora zeae-maydis*): A 1 to 9 visual rating indicating the resistance to Gray Leaf Spot. A higher score indicates a higher resistance. Data are collected only when sufficient selection pressure exists.

GOSWLT=GOSS' WILT (*Corynebacterium nebraskense*): A 1 to 9 visual rating indicating the resistance to Goss' Wilt. A higher score indicates a higher resistance. Data are collected only when sufficient selection pressure exists.

GRAIN TEXTURE: A visual rating used to indicate the appearance of mature grain observed in the middle third of the uppermost ear when well developed. Grain or seed with a hard grain texture is indicated as flint; grain or seed with a soft grain texture is indicted as dent. Medium grain or seed texture may be indicated as flint-dent or intermediate. Other grain textures include flint-like, dent-like, sweet, pop, waxy and flour.

GRNAPP=GRAIN APPEARANCE: This is a 1 to 9 rating for the general appearance of the shelled grain as it is harvested based on such factors as the color of harvested grain, any mold on the grain, and any cracked grain. Higher scores indicate better grain visual quality.

HAPLOID PLANT PART: A plant part or cell having a haploid genotype.

HCBLT=*HELMINTHOSPORIUM CARBONUM* LEAF BLIGHT (*Helminthosporium carbonum*): A 1 to 9 visual rating indicating the resistance to *Helminthosporium* infection. A higher score indicates a higher resistance. Data are collected only when sufficient selection pressure exists.

HD SMT=HEAD SMUT (*Sphacelotheca reiliana*): This indicates the percentage of plants not infected. Data are collected only when sufficient selection pressure exists.

HSKCVR=HUSK COVER: A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

HYBRID VARIETY: A substantially heterozygous hybrid line and minor genetic modifications thereof that retain the overall genetics of the hybrid line.

INBRED: A variety developed through inbreeding or doubled haploidy that preferably comprises homozygous alleles at about 95% or more of its loci. An inbred can be reproduced by selfing or growing in isolation so that the plants can only pollinate with the same inbred variety.

INTROGRESSION: The process of transferring genetic material from one genotype to another.

KERNEL PERICARP COLOR is scored when kernels have dried down and is taken at or about 65 days after 50% silk. Score codes are: Colorless=1; Red with white crown=2; Tan=3; Bronze=4; Brown=5; Light red=6; Cherry red=7.

KER_WT=KERNEL NUMBER PER UNIT WEIGHT (Pounds or Kilograms): The number of kernels in a specific measured weight; determined after removal of extremely small and large kernels.

LINKAGE: Refers to a phenomenon wherein alleles on the same chromosome tend to segregate together more often than expected by chance if their transmission was independent.

LINKAGE DISEQUILIBRIUM: Refers to a phenomenon wherein alleles tend to remain together in linkage groups when segregating from parents to offspring, with a greater frequency than expected from their individual frequencies.

LOCUS: A specific location on a chromosome.

LOCUS CONVERSION (Also called TRAIT CONVERSION): A locus conversion refers to plants within a variety that have been modified in a manner that retains the overall genetics of the variety and further comprises one or more loci with a specific desired trait, such as male sterility, insect resistance, disease resistance or herbicide tolerance or resistance. Examples of single locus conversions include mutant genes, transgenes and native traits finely mapped to a single locus. One or more locus conversion traits may be introduced into a single corn variety.

L/POP=YIELD AT LOW DENSITY: Yield ability at relatively low plant densities on a 1 to 9 relative system with a higher number indicating the hybrid responds well to low plant densities for yield relative to other hybrids. A 1, 5, and 9 would represent very poor, average, and very good yield response, respectively, to low plant density.

LRTLPN=LATE ROOT LODGING: An estimate of the percentage of plants that do not root lodge after anthesis through harvest; plants that lean from the vertical axis at an approximately 30° angle or greater would be considered as root lodged. Data are collected only when sufficient selection pressure exists.

LRTLSC=LATE ROOT LODGING SCORE: Score for severity of plants that lean from a vertical axis at an approximate 30° angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging. Data are collected only when sufficient selection pressure exists.

MALE STERILITY: A male sterile plant is one which produces no viable pollen no (pollen that is able to fertilize the egg to produce a viable seed). Male sterility prevents self pollination. These male sterile plants are therefore useful in hybrid plant production.

MDMCPX=MAIZE DWARF MOSAIC COMPLEX (MDMV=Maize Dwarf Mosaic Virus and MCDV=Maize Chlorotic Dwarf Virus): A 1 to 9 visual rating indicating the resistance to Maize Dwarf Mosaic Complex. A higher score indicates a higher resistance. Data are collected only when sufficient selection pressure exists.

MILKLN=percent milk in mature grain.

MST=HARVEST MOISTURE: The moisture is the actual percentage moisture of the grain at harvest.

NEI DISTANCE: A quantitative measure of percent similarity between two varieties. Nei's distance between varieties A and B can be defined as 1−(2*number alleles in common/(number alleles in A+number alleles in B). For example, if varieties A and B are the same for 95 out of 100 alleles, the Nei distance would be 0.05. If varieties A and B are the same for 98 out of 100 alleles, the Nei distance would be 0.02. Free software for calculating Nei distance is available on the internet at multiple locations. See Nei, Proc Natl Acad Sci, 76:5269-5273 (1979.

NLFBLT=NORTHERN LEAF BLIGHT (*Helminthosporium turcicum* or *Exserohilum turcicum*): A 1 to 9 visual rating indicating the resistance to Northern Leaf Blight. A higher score indicates a higher resistance. Data are collected only when sufficient selection pressure exists.

OILT=GRAIN OIL: Absolute value of oil content of the kernel as predicted by Near-Infrared Transmittance and expressed as a percent of dry matter.

PERCENT IDENTITY: Percent identity as used herein refers to the comparison of the alleles present in two varieties. For example, when comparing two inbred plants to each other, each inbred plant will have the same allele (and therefore be homozygous) at almost all of their loci. Percent identity is determined by comparing a statistically significant number of the homozygous alleles of two varieties. For example, a percent identity of 90% between PH4DAZ and other variety means that the two varieties have the same homozygous alleles at 90% of their loci.

PLANT: As used herein, the term "plant" includes reference to an immature or mature whole plant, including a plant that has been detasseled or from which seed or grain has been removed. Seed or embryo that will produce the plant is also considered to be the plant.

PLANT PART: As used herein, the term "plant part" includes leaves, stems, roots, seed, grain, embryo, pollen, ovules, flowers, ears, cobs, husks, stalks, root tips, anthers, pericarp, silk, tissue, cells and the like. In some embodiments, the plant part contains at least one cell of inbred maize variety PH4DAZ (or a locus conversion thereof) or a hybrid produced from inbred variety PH4DAZ (or a locus conversion thereof).

PLATFORM indicates the variety with the base genetics and the variety with the base genetics comprising locus conversion(s). There can be a platform for the inbred maize variety and the hybrid maize variety.

PLTHT=EDPLTHWT=PLANT HEIGHT: This is a measure of the height of the plant from the ground to the tip of the tassel in inches (PLTHT) or cm.

POLSC=POLLEN SCORE: A 0 to 9 visual rating indicating the amount of pollen shed. The higher the score the more pollen shed.

RM=RELATIVE MATURITY: This is a predicted relative maturity, based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PROT=GRAIN PROTEIN: Absolute value of protein content of the kernel as predicted by Near-Infrared Transmittance and expressed as a percent of dry matter.

RESISTANCE: Synonymous with tolerance. The ability of a plant to withstand exposure to an insect, disease, herbicide or other condition. A resistant plant variety will have a level of resistance higher than a comparable wild-type variety.

RTLDG=ROOT LODGING: Root lodging is the percentage of plants that do not root lodge; plants that lean from the vertical axis at an approximately 30° angle or greater would be counted as root lodged. Data are collected only when sufficient selection pressure exists.

SEED: Fertilized and ripened ovule, consisting of the plant embryo, stored food material, and a protective outer seed coat. Synonymous with grain.

SELF POLLINATION: A plant is self-pollinated if pollen from one flower is transferred to the same or another flower of the same plant.

SIB POLLINATION: A plant is sib-pollinated when individuals within the same family or variety are used for pollination.

SITE SPECIFIC INTEGRATION: Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821.

SLFBLT=SOUTHERN LEAF BLIGHT (*Helminthosporium maydis* or *Bipolaris maydis*): A 1 to 9 visual rating indicating the resistance to Southern Leaf Blight. A higher score indicates a higher resistance. Data are collected only when sufficient selection pressure exists.

SNP=SINGLE-NUCLEOTIDE POLYMORPHISM: is a DNA sequence variation occurring when a single nucleotide in the genome differs between individual plant or plant varieties. The differences can be equated with different alleles, and indicate polymorphisms. A number of SNP markers can be used to determine a molecular profile of an individual plant or plant variety and can be used to compare similarities and differences among plants and plant varieties.

SOURST=SOUTHERN RUST (*Puccinia polysora*): A 1 to 9 visual rating indicating the resistance to Southern Rust. A higher score indicates a higher resistance. Data are collected only when sufficient selection pressure exists.

SPKDSC=EDTASAFDs=TASSEL SPIKELET DENSITY SCORE: The visual rating of how dense spikelets are on the middle to middle third of tassel branches. A higher score on a 1-9 scale indicates higher spikelet density (SPKDSC). On a 3 to 7 scale, 3 is moderately lax, 5 is medium, and 7 is moderately dense.

STAGRN=STAY GREEN: Stay green is the measure of plant health near the time of black layer formation (physiological maturity). A high score indicates better late-season plant health.

STKLDS=STALK LODGING SCORE: A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging. Data are collected only when sufficient selection pressure exists.

STLLPN=LATE STALK LODGING: This is the percent of plants that did not stalk lodge (stalk breakage or crimping) at or around late season harvest (when grain moisture is below 20%) as measured by either natural lodging or pushing the stalks and determining the percentage of plants that break or crimp below the ear. Data are collected only when sufficient selection pressure exists.

STLPCN=STALK LODGING REGULAR: This is an estimate of the percentage of plants that did not stalk lodge (stalk breakage) at regular harvest (when grain moisture is between about 20% and 30%) as measured by either natural lodging or pushing the stalks and determining the percentage of plants that break below the ear. Data are collected only when sufficient selection pressure exists.

STWWLT=Stewart's Wilt (*Erwinia stewartii*): A 1 to 9 visual rating indicating the resistance to Stewart's Wilt. A higher score indicates a higher resistance. Data are collected only when sufficient selection pressure exists.

SSRs: Genetic markers based on polymorphisms in repeated nucleotide sequences, such as microsatellites. A marker system based on SSRs can be informative in linkage analysis relative to other marker systems in that multiple alleles may be present.

TASBRN=TASSEL BRANCH NUMBER: The number of tassel branches, with anthers originating from the central spike.

TASSZ=TASSEL SIZE: A 1 to 9 visual rating was used to indicate the relative size of the tassel. A higher rating means a larger tassel.

TAS WT=TASSEL WEIGHT: This is the average weight of a tassel (grams) just prior to pollen shed.

TILLER=TILLERS: A count of the number of tillers per plot that could possibly shed pollen was taken. Data are given as a percentage of tillers: number of tillers per plot divided by number of plants per plot. A tiller is defined as a secondary shoot that has developed as a tassel capable of shedding pollen.

TSTWT=TEST WEIGHT (ADJUSTED): The measure of the weight of grain in pounds for a given volume (bushel), adjusted for MST less than or equal to 22%.

TSTWTN=TEST WEIGHT (UNADJUSTED): The measure of the weight of the grain in pounds for a given volume (bushel).

VARIETY: A maize line and minor genetic modifications thereof that retain the overall genetics of the line including but not limited to a locus conversion, a mutation, or a somoclonal variant.

YIELD BU/A=YIELD (BUSHELS/ACRE): Yield of the grain at harvest by weight or volume (bushels) per unit area (acre) adjusted to 15% moisture.

YLDADV=YIELD ADVANTAGE. The yield advantage of variety #1 over variety #2 as calculated by: YIELD of variety #1−YIELD variety #2=YIELD ADVANTAGE of variety #1.

YIELDMST=YIELD/MOISTURE RATIO.

YLDSC=YIELD SCORE: A 1 to 9 visual rating was used to give a relative rating for yield based on plot ear piles. The higher the rating the greater visual yield appearance.

YIELDS=Silage Dry Matter Yield (tons/acre @ 100% DM)

MLKYLD=Estimated pounds of milk produced per ton of dry matter fed and is based on utilizing nutrient content and fiber digestibility ADJMLK=Estimated pounds of milk produced per acre of silage dry matter based on an equation and is MLKYLD divided by YIELDS.

SLGPRM=Silage Predicted Relative Maturity

SY30DM=Silage Yield (Tonnage) Adjusted to 30% Dry Matter

PCTMST=Silage Harvest Moisture %

NDFDR=Silage Fiber Digestibility Based on rumen fluid NIRS calibration

NDFDC=Silage Fiber Digestibility Based on rumen fluid NIRS calibration

Phenotypic Characteristics of PH4DAZ

Inbred maize variety PH4DAZ may be used as a male or female in the production of the first generation F1 hybrid. The variety has shown uniformity and stability within the limits of environmental influence for all the traits as described in the Variety Description Information (Table 1, found at the end of the section). The variety has been self-pollinated and ear-rowed a sufficient number of generations with careful attention paid to uniformity of plant type to ensure sufficient homozygosity and phenotypic stability for use in commercial hybrid seed production. The variety has been increased both by hand and in isolated fields with continued observation for uniformity. No variant traits have been observed or are expected in PH4DAZ.

Genotypic Characteristics of PH4DAZ

In addition to phenotypic observations, a plant can also be identified by its genotype. The genotype of a plant can be characterized through a genetic marker profile.

As a result of inbreeding, PH4DAZ is substantially homozygous. This homozygosity can be characterized at the loci shown in a marker profile. An F1 hybrid made with PH4DAZ would substantially comprise the marker profile of PH4DAZ. This is because an F1 hybrid is the sum of its inbred parents, e.g., if one inbred parent is homozygous for allele x at a particular locus, and the other inbred parent is homozygous for allele y at that locus, the F1 hybrid will be xy (heterozygous) at that locus. A genetic marker profile can therefore be used to identify hybrids comprising PH4DAZ as a parent, since such hybrids will comprise two sets of alleles, one set of which will be from PH4DAZ. The determination of the male set of alleles and the female set of alleles may be made by profiling the hybrid and the pericarp of the hybrid seed, which is composed of maternal parent cells. One way to obtain the paternal parent profile is to subtract the pericarp profile from the hybrid profile.

Subsequent generations of progeny produced by selection and breeding are expected to be of genotype xx (homozygous), yy (homozygous), or xy (heterozygous) for these locus positions. When the F1 plant is used to produce an inbred, the resulting inbred should be either x or y for that allele.

Therefore, in accordance with the above, an embodiment is a PH4DAZ progeny maize plant or plant part that is a first generation (F1) hybrid maize plant comprising two sets of alleles, wherein one set of the alleles is the same as PH4DAZ at substantially all loci. A maize cell wherein one set of the alleles is the same as PH4DAZ at substantially all loci is also provided. This maize cell may be a part of a hybrid seed, plant or plant part produced by crossing PH4DAZ with another maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry et al. (2002), "Assessing Probability of Ancestry Using Simple Sequence Repeat Profiles: Applications to Maize Hybrids and Inbreds", Genetics, 2002, 161:813-824, and Berry et al. (2003), "Assessing Probability of Ancestry Using Simple Sequence Repeat Profiles: Applications to Maize Inbred Lines and Soybean Varieties", Genetics, 2003, 165: 331-342.

Particular markers used for these purposes may include any type of marker and marker profile which provides a means of distinguishing varieties. A genetic marker profile can be used, for example, to identify plants of the same variety or related varieties or to determine or validate a pedigree. In addition to being used for identification of maize variety PH4DAZ, a hybrid produced through the use of PH4DAZ, and the identification or verification of pedigree for progeny plants produced through the use of PH4DAZ, a genetic marker profile is also useful in developing a locus conversion of PH4DAZ.

Methods of isolating nucleic acids from maize plants and methods for performing genetic marker profiles using SNP and SSR polymorphisms are well known in the art. SNPs are genetic markers based on a polymorphism in a single nucleotide. A marker system based on SNPs can be highly informative in linkage analysis relative to other marker systems in that multiple alleles may be present.

A method comprising isolating nucleic acids, such as DNA, from a plant, a plant part, plant cell or a seed of the maize plants disclosed herein is provided. The method can include mechanical, electrical and/or chemical disruption of the plant, plant part, plant cell or seed, contacting the disrupted plant, plant part, plant cell or seed with a buffer or solvent, to produce a solution or suspension comprising nucleic acids, optionally contacting the nucleic acids with a precipitating agent to precipitate the nucleic acids, optionally extracting the nucleic acids, and optionally separating the nucleic acids such as by centrifugation or by binding to beads or a column, with subsequent elution, or a combination thereof. If DNA is being isolated, an RNase can be included in one or more of the method steps. The nucleic acids isolated can comprise all or substantially all of the genomic DNA sequence, all or substantially all of the chromosomal DNA sequence or all or substantially all of the coding sequences (cDNA) of the plant, plant part, or plant cell from which they were isolated. The amount and type of nucleic acids isolated may be sufficient to permit whole genome sequencing of the plant from which they were isolated or chromosomal marker analysis of the plant from which they were isolated.

The methods can be used to produce nucleic acids from the plant, plant part, seed or cell, which nucleic acids can be, for example, analyzed to produce data. The data can be recorded. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some examples, the nucleic acids produced can be sequenced or contacted with markers to produce a genetic profile, a molecular profile, a marker profile, a haplotype, or any combination thereof. In some examples, the genetic profile or nucleotide sequence is recorded on a computer readable medium. In other examples, the methods may further comprise using the nucleic acids produced from plants, plant parts, plant cells or seeds in a plant breeding program, for example in making crosses, selection and/or advancement decisions in a breeding program. Crossing includes any type of plant breeding crossing method, including but not limited to crosses to produce hybrids, outcrossing, selfing, backcrossing, locus conversion, introgression and the like.

Favorable genotypes and or marker profiles, optionally associated with a trait of interest, may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis. PH4DAZ and its plant parts can be identified through a molecular marker profile. Such plant parts may be either diploid or haploid. The plant part includes at least one cell of the plant from which it was obtained, such as a diploid cell, a haploid cell or a somatic cell. Also provided are plants and plant parts substantially benefiting from the use of variety PH4DAZ in their development, such as variety PH4DAZ comprising a locus conversion.

Comparing PH4DAZ to Other Inbreds

A breeder uses various methods to help determine which plants should be selected from segregating populations and ultimately which inbred varieties will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred varieties and hybrid combinations are significantly better or different for one or more traits of interest. Experimental design methods are used to assess error so that differences between two inbred varieties or two hybrid varieties can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is a significant difference between the two traits expressed by those varieties. For example, see Fehr, Walt, Principles of Cultivar Development, p. 261-286 (1987). Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide tolerance, insect or disease resistance. A locus conversion of PH4DAZ for herbicide tolerance should be compared with an isogenic counterpart in the absence of the converted trait. In addition, a locus conversion for insect or disease resistance should be compared to the isogenic counterpart, in the absence of disease pressure or insect pressure.

Development of Maize Hybrids using PH4DAZ

A single cross maize hybrid results from the cross of two inbred varieties, each of which has a genotype that complements the genotype of the other. A hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

PH4DAZ may be used to produce hybrid maize. One such embodiment is the method of crossing maize variety PH4DAZ with another maize plant, such as a different maize variety, to form a first generation F1 hybrid seed. The first generation F1 hybrid seed, plant and plant part produced by this method are provided. The first generation F1 seed, plant and plant part will comprise an essentially complete set of the alleles of variety PH4DAZ. One of ordinary skill in the art can utilize molecular methods to identify a particular F1 hybrid plant produced using variety PH4DAZ. Further, one of ordinary skill in the art may also produce F1 hybrids with transgenic, male sterile and/or locus conversions of variety PH4DAZ.

The development of a maize hybrid in a maize plant breeding program involves three steps: (1) the selection of plants from various germplasm pools for initial breeding crosses; (2) the selfing of the selected plants from the breeding crosses for several generations to produce a series of varieties, such as PH4DAZ, which, although different from each other, breed true and are highly uniform; and (3) crossing the selected varieties with different varieties to produce the hybrids. During the inbreeding process in maize, the vigor of the varieties decreases, and so one would not be likely to use PH4DAZ directly to produce grain. However, vigor is restored when PH4DAZ is crossed to a different inbred variety to produce a commercial F1 hybrid. A consequence of the homozygosity and homogeneity of the inbred variety is that the hybrid between a defined pair of inbreds may be reproduced indefinitely as long as the homogeneity of the inbred parents is maintained.

PH4DAZ may be used to produce a single cross hybrid, a double cross hybrid, or a three-way hybrid. A single cross hybrid is produced when two inbred varieties are crossed to produce the F1 progeny. A double cross hybrid is produced from four inbred varieties crossed in pairs (A×B and C×D) and then the two F1 hybrids are crossed again (A×B)×(C× D). A three-way cross hybrid is produced from three inbred varieties where two of the inbred varieties are crossed (A×B) and then the resulting F1 hybrid is crossed with the third inbred (A×B)×C. In each case, pericarp tissue from the female parent will be a part of and protect the hybrid seed.

Molecular data from PH4DAZ may be used in a plant breeding process. Nucleic acids may be isolated from a seed of PH4DAZ or from a plant, plant part, or cell produced by growing a seed of PH4DAZ, or from a seed of PH4DAZ with a locus conversion, or from a plant, plant part, or cell of PH4DAZ with a locus conversion. One or more polymorphisms may be isolated from the nucleic acids. A plant having one or more of the identified polymorphisms may be selected and used in a plant breeding method to produce another plant.

Combining Ability of PH4DAZ

Combining ability of a variety, as well as the performance of the variety per se, is a factor in the selection of improved maize inbreds. Combining ability refers to a variety's contribution as a parent when crossed with other varieties to form hybrids. The hybrids formed for the purpose of selecting superior varieties may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the varieties.

General combining ability provides an overall score for the inbred over a large number of test crosses. Specific combining ability provides information on hybrid combinations formed by PH4DAZ and a specific inbred parent. A variety such as PH4DAZ which exhibits good general combining ability may be used in a large number of hybrid combinations.

Hybrid comparisons represent specific hybrid crosses with PH4DAZ and a comparison of these specific hybrids with other hybrids with favorable characteristics. These comparisons illustrate the good specific combining ability of PH4DAZ. A specific hybrid for which PH4DAZ is a parent is compared with other hybrids. Numerous species of the genus of F1 hybrids created with PH4DAZ have been reduced to practice. These comparisons illustrate the good specific combining ability of PH4DAZ or PH4DAZ comprising locus conversions.

Introduction of a new trait or locus into PH4DAZ

Inbred PH4DAZ represents a new base genetic variety into which a new locus or trait may be introduced or introgressed. Transformation and backcrossing represent two methods that can be used to accomplish such an introgression. The term locus conversion is used to designate the product of such an introgression.

A backcross or locus conversion of PH4DAZ occurs when DNA sequences are introduced through backcrossing (Hallauer et al. in Corn and Corn Improvement, Sprague and Dudley, Third Ed. 1998), with PH4DAZ utilized as the recurrent parent. Both naturally occurring, modified and transgenic DNA sequences may be introduced through backcrossing techniques. A backcross or locus conversion may produce a plant with a trait or locus conversion in at least one or more backcrosses, including at least 2 backcrosses, at least 3 backcrosses, at least 4 backcrosses, at least 5 backcrosses and the like. Molecular marker assisted breeding or selection may be utilized to reduce the number of backcrosses necessary to achieve the backcross conversion. For example, see Openshaw et al., "Marker-assisted Selection in Backcross Breeding," in: Proceedings Symposium of the Analysis of Molecular Data, August 1994, Crop Science Society of America, Corvallis, Oreg., which demonstrated that a backcross locus conversion can be made in as few as two backcrosses.

The complexity of the backcross conversion method depends on the type of trait being transferred (a single gene or closely linked genes compared to unlinked genes), the level of expression of the trait, the type of inheritance (cytoplasmic or nuclear), dominant or recessive trait expression, and the types of parents included in the cross. It is understood by those of ordinary skill in the art that for single locus or gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, waxy starch, sterility (nuclear and cytoplasmic), fertility restoration, grain color (white), nutritional enhancements, drought tolerance, nitrogen utilization, altered fatty acid profile, increased digestibility, low phytate, industrial enhancements, disease resistance (bacterial, fungal, or viral), insect resistance, and herbicide tolerance or resistance. A locus conversion, also called a trait conversion, can be a native trait or a transgenic trait. In addition, an recombination site itself, such as an FRT site, Lox site, or other site specific integration site may be inserted by backcrossing and utilized for direct insertion of one or more genes of interest into a specific plant variety. A single locus may contain several transgenes, such as a transgene for disease resistance that, in the same expression vector, also contains a transgene for herbicide tolerance or resistance. The gene for herbicide tolerance or resistance may be used as a selectable marker and/or as a phenotypic trait. A single locus conversion of a site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross or locus conversion may result from either the transfer of a dominant allele or a recessive allele. Selection of progeny containing the trait of interest can be accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype and/or genotype of the recurrent parent. While occasionally additional polynucleotide sequences or genes may be transferred along with the backcross conversion, the backcross conversion variety "fits into the same hybrid combination as the recurrent parent inbred variety and contributes the effect of the additional locus added through the backcross." Poehlman et al (1995) *Breeding Field Crop*, 4th Ed., Iowa State University Press, Ames, Iowa, pp. 132-155 and 321-344. When one or more traits are introgressed into the variety a difference in quantitative agronomic traits, such as yield or dry down, between the variety and an introgressed version of the variety in some environments may occur. For example, the introgressed version may provide a net yield increase in environments where the trait provides a benefit, such as when a variety with an introgressed trait for insect resistance is grown in an environment where insect pressure exists, or when a variety with herbicide tolerance is grown in an environment where herbicide is used.

One process for adding or modifying a trait or locus in maize variety PH4DAZ comprises crossing PH4DAZ plants grown from PH4DAZ seed with plants of another maize variety that comprise the desired trait or locus, selecting F1 progeny plants that comprise the desired trait or locus to produce selected F1 progeny plants, crossing the selected progeny plants with the PH4DAZ plants to produce backcross progeny plants, selecting for backcross progeny plants that have the desired trait or locus and the phenotypic characteristics of maize variety PH4DAZ to produce selected backcross progeny plants; and backcrossing to PH4DAZ one or more times in succession to produce backcross progeny plants that comprise the trait or locus.

The modified PH4DAZ or a plant otherwise derived from PH4DAZ may be further characterized as having all or essentially all of the phenotypic characteristics, or essentially all of the morphological and physiological characteristics of maize variety PH4DAZ, such as those listed in Table 1 and/or may be characterized by percent identity to PH4DAZ as determined by molecular markers, such as SSR markers or SNP markers. By essentially all of the phenotypic or morphological and physiological characteristics, it is meant that all of the characteristics of a plant are recovered that are otherwise present when compared in the same environment, other than an occasional variant trait that might arise during backcrossing or direct introduction of a transgene. Such traits may be determined, for example, relative to the traits listed in Table 1 as determined at the 5% significance level when grown under the same environmental conditions.

In addition, the above process and other similar processes described herein may be used to produce F1 hybrid maize seed by adding a step at the end of the process that comprises crossing PH4DAZ with the locus conversion with a different maize plant and harvesting the resultant F1 hybrid maize seed.

Traits are also used by those of ordinary skill in the art to characterize progeny. Traits are commonly evaluated at a significance level, such as a 1%, 5% or 10% significance level, when measured in plants grown in the same environmental conditions.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

PH4DAZ can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile designated PH4DAZ may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's and the male sterility trait is routinely backcrossed into inbred varieties.

There are several methods of conferring genetic male sterility available, such as multiple mutant genes at separate locations within the genome that confer male sterility, as disclosed in U.S. Pat. Nos. 4,654,465 and 4,727,219. and chromosomal translocations as described in U.S. Pat. Nos. 3,861,709 and 3,710,511. In addition to these methods U.S. Pat. No. 5,432,068 describes a system of nuclear male sterility which includes: identifying a gene which is needed for male fertility; silencing this native gene which is needed for male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene needed for fertility is identified and an antisense to that gene is inserted in the plant (see EP 89/3010153.8 publication no. 329,308 and PCT application PCT/CA90/00037 published as WO 90/08828).

Another system for controlling male sterility makes use of gametocides. Gametocides are not a genetic system, but rather a topical application of chemicals. These chemicals affect cells that are needed for male fertility. The application of these chemicals affects fertility in the plants only for the growing season in which the gametocide is applied (see U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be one of the inbred varieties used to produce the hybrid. Though the possibility of PH4DAZ being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, or other characteristics.

Identification of these self-pollinated varieties can also be accomplished through molecular marker analyses. Through these technologies, the homozygosity of the self-pollinated variety can be verified by analyzing allelic composition at various loci along the genome. Those methods allow for rapid identification of the plants disclosed herein.

Transformation

Transgenes and transformation methods facilitate engineering of the genome of plants to contain and express heterologous genetic elements, such as foreign genetic elements, or additional copies of endogenous elements, or modified versions of native or endogenous genetic elements in order to alter at least one trait of a plant in a specific manner. Any sequences, such as DNA, whether from a different species or from the same species, which have been stably inserted into a genome using transformation are referred to herein collectively as "transgenes" and/or "transgenic events". Transgenes can be moved from one genome to another using breeding techniques which may include crossing, backcrossing or double haploid production. In some embodiments, a transformed variant of PH4DAZ may comprise at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Transformed versions of the claimed maize variety PH4DAZ as well as hybrid combinations containing and inheriting the transgene thereof are provided. F1 hybrid seed are provided which are produced by crossing a different maize plant with maize variety PH4DAZ comprising a transgene introduced into maize variety PH4DAZ by backcrossing or genetic transformation and is inherited by the F1 hybrid seed.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

In general, methods to transform, modify, edit or alter plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. As an example, a genetically modified plant variety is generated using "custom" or engineered endonucleases such as meganucleases produced to modify plant genomes (see e.g., WO 2009/114321; Gao et al. (2010) Plant Journal 1:176-187). Another site-directed engineering method is through the use of zinc finger domain recognition coupled with the restriction properties of restriction enzyme. See e.g., Urnov, et al., (2010) Nat Rev Genet. 11(9):636-46; Shukla, et al., (2009) Nature 459 (7245):437-41. A transcription activator-like (TAL) effector-DNA modifying enzyme (TALE or TALEN) is also used to engineer changes in plant genome. See e.g., US20110145940, Cermak et al., (2011) Nucleic Acids Res. 39(12) and Boch et al., (2009), Science 326(5959): 1509-12. Site-specific modification of plant genomes can also be performed using the bacterial type II CRISPR (clustered regularly interspaced short palindromic repeats)/Cas (CRISPR-associated) system. See e.g., Belhaj et al., (2013), Plant Methods 9: 39; The Cas9/guide RNA-based system allows targeted cleavage of genomic DNA guided by a customizable small noncoding RNA in plants (see e.g., WO 2015026883A1).

Plant transformation methods may involve the construction of an expression vector. Such a vector comprises a DNA sequence that contains a gene under the control of or operatively linked to a regulatory element, for example a promoter. The vector may contain one or more genes and one or more regulatory elements.

A transgenic event which has been stably engineered into the germ cell line of a particular maize plant using transformation techniques, could be moved into the germ cell line of another variety using traditional breeding techniques that are well known in the plant breeding arts. For example, a backcrossing approach is commonly used to move a transgenic event from a transformed maize plant to another variety, and the resulting progeny would then comprise the transgenic event(s). Also, if an inbred variety was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. Nos. 6,118,055 and 6,284,953. In addition, transformability of a variety can be increased by introgressing the trait of high transformability from another variety known to have high transformability, such as Hi-II. See US Patent Publication US2004/0016030.

With transgenic or genetically modified plants, a foreign protein can be produced in commercial quantities. Thus, techniques for the selection and propagation of transformed plants, which are well understood in the art, yield a plurality of transgenic or genetically modified plants that are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92-6 (1981).

Transgenic events can be mapped by one of ordinary skill in the art and such techniques are well known to those of ordinary skill in the art. For exemplary methodologies in this regard, see for example, Glick and Thompson, Methods in Plant Molecular Biology and Biotechnology 269-284 (CRC Press, Boca Raton, 1993).

Plants can be genetically engineered or modified to express various phenotypes of agronomic interest. Through the transformation or modification of maize the expression of genes can be altered to enhance disease resistance, insect resistance, herbicide tolerance, agronomic traits, grain quality and other traits. Transformation can also be used to insert DNA sequences which control or help control male-sterility. DNA sequences native to maize as well as non-native DNA sequences can be transformed into maize and used to alter levels of native or non-native proteins. Various promoters, targeting sequences, enhancing sequences, and other DNA sequences can be inserted into the maize genome for the purpose of altering the expression of proteins. Reduction of the activity of specific genes (also known as gene silencing, or gene suppression) is desirable for several aspects of genetic engineering in plants.

Many techniques for gene silencing are well known to one of skill in the art, including but not limited to knock-outs (such as by insertion of a transposable element such as mu (Vicki Chandler, *The Maize Handbook* Ch. 118 (Springer-Verlag 1994) or other genetic elements such as a FRT, Lox or other site specific integration site, antisense technology (see, e.g., Sheehy et al. (1988) *PNAS* USA 85:8805-8809; and U.S. Pat. Nos. 5,107,065; 5,453,566; and 5,759,829); co-suppression (e.g., Taylor (1997) *Plant Cell* 9:1245; Jorgensen (1990) *Trends Biotech.* 8(12):340-344; Flavell (1994) *PNAS* USA 91:3490-3496; Finnegan et al. (1994) *Bio/Technology* 12: 883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS* USA 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); MicroRNA (Aukerman and Sakai (2003) *Plant Cell* 15:2730-2741); ribozymes (Steinecke et al. (1992) *EMBO J.* 11:1525; and Perriman et al. (1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary nucleotide sequences that may be altered by genetic engineering include, but are not limited to, those categorized below.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporium fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*), McDowell and Woffenden, (2003) Trends Biotechnol. 21(4): 178-83 and Toyoda et al., (2002) Transgenic Res. 11(6):567-82. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other non-limiting examples of *Bacillus thuringiensis* transgenes being genetically engineered are given in the following patents and patent publications: U.S. Pat. Nos. 5,188,960; 5,689,052; 5,880,275; 5,986,177; 7,105,332; 7,208,474, 7,329,736; 7,449,552, 7,468,278, 7,510,878, 7,521,235, 7,605,304, 7,696,412, 7,629,504, 7,772,465, 7,790,846, 7,858,849, WO 91/14778; WO 99/31248; WO 01/12731; WO 99/24581; and WO 97/40162.

(C) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(D) An insect-specific peptide which, upon expression, disrupts the physiology of the affected pest. For example, see Regan, *J. Biol. Chem.* 269: 9 (1994) (expression cloning yields DNA coding for insect diuretic hormone receptor); Pratt et al., *Biochem. Biophys. Res. Comm.* 163: 1243 (1989) (an allostatin is identified in *Diploptera puntata*); Chattopadhyay et al. (2004) Critical Reviews in Microbiology 30 (1): 33-54 2004; Zjawiony (2004) J Nat Prod 67 (2): 300-310; Carlini and Grossi-de-Sa (2002) Toxicon, 40 (11): 1515-1539; Ussuf et al. (2001) Curr Sci. 80 (7): 847-853; and Vasconcelos and Oliveira (2004) Toxicon 44 (4): 385-403. See also U.S. Pat. No. 5,266,317 disclosing genes encoding insect-specific toxins.

(E) An enzyme responsible for a hyperaccumulation of a monoterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673

(1993), who provide the nucleotide sequence of the parsley ubi4-2 polyubiquitin gene, and U.S. Pat. Nos. 6,563,020; 7,145,060 and 7,087,810.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 and U.S. Pat. No. 5,580,852 disclosure of peptide derivatives of Tachyplesin which inhibit fungal plant pathogens) and PCT application WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), which shows that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995), Pieterse and Van Loon (2004) Curr. Opin. Plant Bio. 7(4):456-64 and Somssich (2003) Cell 113(7):815-6.

(P) Antifungal genes (Cornelissen and Melchers, Pl. Physiol. 101:709-712, (1993) and Parijs et al., Planta 183: 258-264, (1991) and Bushnell et al., Can. J. of Plant Path. 20(2):137-149 (1998). Also see U.S. application Ser. Nos. 09/950,933; 11/619,645; 11/657,710; 11/748,994; 11/774, 121 and U.S. Pat. Nos. 6,891,085 and 7,306,946.

(Q) Detoxification genes, such as for fumonisin, beauvericin, moniliformin and zearalenone and their structurally related derivatives. For example, see U.S. Pat. Nos. 5,716, 820; 5,792,931; 5,798,255; 5,846,812; 6,083,736; 6,538, 177; 6,388,171 and 6,812,380.

(R) Cystatin and cysteine proteinase inhibitors. See U.S. Pat. No. 7,205,453.

(S) Defensin genes. See WO03000863 and U.S. Pat. Nos. 6,911,577; 6,855,865; 6,777,592 and 7,238,781.

(T) Genes conferring resistance to nematodes. See e.g. PCT Application WO96/30517; PCT Application WO93/19181, WO 03/033651 and Urwin et al., Planta 204:472-479 (1998), Williamson (1999) Curr Opin Plant Bio. 2(4):327-31; and U.S. Pat. Nos. 6,284,948 and 7,301,069.

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker et al, *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035.

(W) Genes that confer resistance to *Colletotrichum*, such as described in US Patent Publication No. US20090035765. This includes the Rcg locus that may be utilized as a single locus conversion.

2. Transgenes that Confer Tolerance to a Herbicide, for example:

(A) A herbicide that inhibits the growing point or meristem, such as an imidazolinone or a sulfonylurea. Exemplary genes in this category code for mutant acetolactate synthase (ALS) and acetohydroxyacid synthase (AHAS) enzyme as described, for example, in U.S. Pat. Nos. 5,605,011; 5,013, 659; 5,141,870; 5,767,361; 5,731,180; 5,304,732; 4,761, 373; 5,331,107; 5,928,937; and 5,378,824; US Patent Publication No. 20070214515, and international publication WO 96/33270.

(B) Glyphosate (tolerance imparted by aroA genes and mutant 5-enolpyruvl-3-phosphikimate synthase (EPSP) and) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835, which discloses the nucleotide sequence of a form of EPSPS which can confer glyphosate tolerance. U.S. Pat. No. 5,627,061 also describes genes encoding EPSPS enzymes. See also U.S. Pat. Nos. 6,566,587; 6,338,961; 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE. 36,449; RE 37,287; and 5,491,288; and international publications EP1173580; WO 01/66704; EP1173581 and EP1173582.

Glyphosate tolerance is also imparted to plants that express a gene that encodes a glyphosate oxido-reductase enzyme as described more fully in U.S. Pat. Nos. 5,776,760 and 5,463,175. In addition glyphosate tolerance can be imparted to plants by the over expression of genes encoding glyphosate N-acetyltransferase. See, for example, US2004/0082770; US2005/0246798; and US2008/0234130. A DNA molecule encoding a mutant aroA gene can be obtained under ATCC accession No. 39256, and the nucleotide sequence of the mutant gene is disclosed in U.S. Pat. No. 4,769,061. EP Patent Application No. 0333033 and U.S. Pat. No. 4,975,374 disclose nucleotide sequences of glutamine synthetase genes which confer tolerance to herbicides such as L-phosphinothricin. The nucleotide sequence of a phosphinothricin-acetyl-transferase gene is provided in EP Patent Nos. 0242246 and 0242236. See also, U.S. Pat. Nos. 5,969, 213; 5,489,520; 5,550,318; 5,874,265; 5,919,675; 5,561, 236; 5,648,477; 5,646,024; 6,177,616 B1; and 5,879,903. Exemplary genes conferring resistance to phenoxy propionic acids, cyclohexanediones and cyclohexones, such as sethoxydim and haloxyfop, are the Acc1-S1, Acc1-S2 and Acc1-S3 genes.

(C) A herbicide that inhibits photosynthesis, such as a triazine (psbA and gs+ genes) and a benzonitrile (nitrilase gene) such as bromoxynil. Przibilla et al., *Plant Cell* 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442.

(D) Other genes that confer tolerance to herbicides include: a gene encoding a chimeric protein of rat cytochrome P4507A1 and yeast NADPH-cytochrome P450 oxidoreductase, genes for glutathione reductase and superoxide dismutase, and genes for various phosphotransferases.

(E) A herbicide that inhibits protoporphyrinogen oxidase (protox or PPO) is necessary for the production of chlorophyll, which is necessary for all plant survival. The protox enzyme serves as the target for a variety of herbicidal compounds. PPO-inhibitor herbicides can inhibit growth of all the different species of plants present, causing their total destruction. The development of plants containing altered protox activity which are tolerant to these herbicides are described, for example, in U.S. Pat. Nos. 6,288,306 B1; 6,282,837 B1; and 5,767,373; and international patent publication WO 01/12825.

(F) Dicamba (3,6-dichloro-2-methoxybenzoic acid) is an organochloride derivative of benzoic acid which functions by increasing plant growth rate such that the plant dies.

3. Transgenes that Confer or Contribute to an Altered Grain Characteristic, Such as:

(A) Altered fatty acids, for example, by (i) Down-regulation of stearoyl-ACP desaturase to increase stearic acid content of the plant. See Knultzon et al., *Proc. Natl. Acad. Sci. USA* 89: 2624 (1992) and WO99/64579 (Genes for Desaturases to Alter Lipid Profiles in Corn), (ii) Elevating oleic acid via FAD-2 gene modification and/or decreasing linolenic acid via FAD-3 gene modification (see U.S. Pat. Nos. 6,063,947; 6,323,392; 6,372,965 and WO 93/11245), (iii) Altering linolenic or linoleic acid content, such as in WO 01/12800, (iv) Altering LEC1, AGP, Dek1, Superal1, mi1ps, various Ipa genes such as Ipa1, Ipa3, hpt or hggt. For example, see WO 02/42424, WO 98/22604, WO 03/011015, WO02/057439, WO03/011015, U.S. Pat. Nos. 6,423,886, 6,197, 561, 6,825,397, and U.S. Application Serial Nos. US2003/0079247, US2003/0204870, and Rivera-Madrid, R. et al. Proc. Natl. Acad. Sci. 92:5620-5624 (1995).

B) Altered phosphate content, for example, by the (i) Introduction of a phytase-encoding gene would enhance breakdown of phytate, adding more free phosphate to the transformed plant. For example, see Van Hartingsveldt et al., *Gene* 127: 87 (1993), for a disclosure of the nucleotide sequence of an *Aspergillus niger* phytase gene.

(ii) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 05/113778 and/or by altering inositol kinase activity as in WO 02/059324, US2003/0009011, WO 03/027243, US2003/0079247, WO 99/05298, U.S. Pat. Nos. 6,197,561, 6,291,224, 6,391,348, WO2002/059324, US2003/0079247, Wo98/45448, WO99/55882, WO01/04147.

(C) Altered carbohydrates affected, for example, by altering a gene for an enzyme that affects the branching pattern of starch or, a gene altering thioredoxin such as NTR and/or TRX (see. (See U.S. Pat. No. 6,531,648) and/or a gamma zein knock out or mutant such as cs27 or TUSC27 or en27 (See U.S. Pat. No. 6,858,778 and US2005/0160488, US2005/0204418). See Shiroza et al., J. Bacteriol. 170: 810 (1988) (nucleotide sequence of *Streptococcus mutans* fructosyltransferase gene), Steinmetz et al., Mol. Gen. Genet. 200: 220 (1985) (nucleotide sequence of *Bacillus subtilis* levansucrase gene), Pen et al., Bio/Technology 10: 292 (1992) (production of transgenic plants that express *Bacillus licheniformis* alpha-amylase), Elliot et al., Plant Molec. Biol. 21: 515 (1993) (nucleotide sequences of tomato invertase genes), Søgaard et al., J. Biol. Chem. 268: 22480 (1993) (site-directed mutagenesis of barley alpha-amylase gene), and Fisher et al., Plant Physiol. 102: 1045 (1993) (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US2004/0034886 and WO 00/68393 involving the manipulation of antioxidant levels, and WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US2003/0163838, US2003/0150014, US2004/0068767, U.S. Pat. No. 6,803,498, WO01/79516.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is needed for male fertility; silencing this native gene which is needed for male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

(A) Introduction of a deacetylase gene under the control of a tapetum-specific promoter and with the application of the chemical N—Ac-PPT (WO 01/29237).

(B) Introduction of stamen-specific promoters (WO 92/13956, WO 92/13957).

(C) Introduction of the barnase and the barstar gene (Paul et al. Plant Mol. Biol. 19:611-622, 1992).

For additional examples of nuclear male and female sterility systems and genes, see also, U.S. Pat. Nos. 5,859,341; 6,297,426; 5,478,369; 5,824,524; 5,850,014; and 6,265,640.

5. Genes that create a site for site specific DNA integration. This includes the introduction of FRT sites that may be used in the FLP/FRT system and/or Lox sites that may be used in the Cre/Loxp system. For example, see Lyznik, et al., Site-Specific Recombination for Genetic Engineering in Plants, Plant Cell Rep (2003) 21:925-932 and WO 99/25821. Other systems that may be used include the Gin recombinase of phage Mu (Maeser et al., 1991; Vicki Chandler, *The Maize Handbook* Ch. 118 (Springer-Verlag 1994), the Pin recombinase of *E. coli* (Enomoto et al., 1983), and the R/RS system of the pSR1 plasmid (Araki et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see: WO 00/73475 where water use efficiency is altered through alteration of malate; U.S. Pat. Nos. 5,892,009; 5,965,705; 5,929,305; 5,891,859; 6,417,428; 6,664,446; 6,706,866; 6,717,034; 6,801,104; WO2000060089; WO2001026459; WO2001035725; WO2001034726; WO2001035727; WO2001036444; WO2001036597; WO2001036598; WO2002015675; WO2002017430; WO2002077185; WO2002079403; WO2003013227; WO2003013228; WO2003014327; WO2004031349; WO2004076638; WO9809521; and WO9938977 describing genes, including CBF genes and transcription factors effective in mitigating the negative effects of freezing, high salinity, and drought on plants, as well as conferring other positive effects on plant phenotype; US2004/0148654 and WO01/36596 where abscisic acid is altered in plants resulting in improved plant phenotype such as increased yield and/or increased tolerance to abiotic stress; WO2000/006341, WO04/090143, U.S. application Ser. Nos. 10/817,483 and 09/545,334 where cytokinin expression is modified resulting in plants with increased stress tolerance, such as drought tolerance, and/or increased yield. Also see WO0202776, WO2003052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see US20040128719, US20030166197 and WO200032761. For plant transcription factors or transcriptional regulators of abiotic stress, see e.g. US20040098764 or US20040078852.

Other genes and transcription factors that affect plant growth and agronomic traits such as yield, flowering, plant growth and/or plant structure, can be introduced or introgressed into plants, see e.g. WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht), WO2004076638 and WO2004031349 (transcription factors).

Using PH4DAZ to Develop Another Maize Plant

Maize varieties such as PH4DAZ are typically developed for use in the production of hybrid maize varieties. However, varieties such as PH4DAZ also provide a source of breeding material that may be used to develop new maize inbred varieties. Plant breeding techniques known in the art and used in a maize plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred varieties, the crossing of these varieties, and the evaluation of the crosses. There are many analytical methods available to evaluate the result of a cross. The oldest and most traditional method of analysis is the observation of phenotypic traits but genotypic analysis may also be used.

Methods for producing a maize plant by crossing a first parent maize plant with a second parent maize plant wherein either the first or second parent maize plant is a maize plant of the variety PH4DAZ are provided. The other parent may be any other maize plant, such as another inbred variety or a plant that is part of a synthetic or natural population. Any such methods may be used with the maize variety PH4DAZ such as selfing, sibbing, backcrosses, mass selection, pedigree breeding, bulk selection, hybrid production, crosses to populations, and the like. These methods are well known in the art and some of the more commonly used breeding methods are described below.

Pedigree Breeding

Pedigree breeding starts with the crossing of two genotypes, such as PH4DAZ and one other inbred variety having one or more desirable characteristics that is lacking or which complements PH4DAZ. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: F1→F2; F2→F3; F3→F4; F4→F5; etc. After a sufficient amount of inbreeding, successive filial generations will serve to increase seed of the developed inbred. Preferably, the inbred variety comprises homozygous alleles at about 95% or more of its loci.

Recurrent Selection and Mass Selection

Recurrent selection is a method used in a plant breeding program to improve a population of plants. PH4DAZ is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross pollinated with each other to form progeny for another population. This population is planted and again superior plants are selected to cross pollinate with each other. Recurrent selection is a cyclical process and can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

PH4DAZ is suitable for use in mass selection. Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation Breeding

Mutation breeding is one of many methods that could be used to introduce new traits into PH4DAZ. PH4DAZ is suitable for use in a mutation breeding program. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. In addition, mutations created in other varieties may be used to produce a backcross conversion of PH4DAZ that comprises such mutation.

Production of Double Haploids

The production of double haploids can also be used for the development of inbreds in the breeding program. For example, an F1 hybrid for which PH4DAZ is a parent can be used to produce double haploid plants. Double haploids are produced by the doubling of a set of chromosomes (1N) from a heterozygous plant to produce a completely homozygous individual. For example, see Wan et al., Theoretical and Applied Genetics, 77:889-892, 1989 and US Patent Publication No. 2003/0005479. This can be advantageous because the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected variety (as female) with an inducer variety. Such inducer varieties for maize include Stock 6 (Coe, 1959, *Am. Nat.* 93:381-382; Sharkar and Coe, 1966, *Genetics* 54:453-464) RWS (available online from the Universität Hohenheim), KEMS (Deimling, Roeber, and Geiger, 1997, *Vortr. Pflanzenzuchtg* 38:203-224), KMS and ZMS (Chalyk, Bylich and Chebotar, 1994, *MNL* 68:47; Chalyk and Chebotar, 2000, *Plant Breeding* 119:363-364), and indeterminate gametophyte (ig) mutation (Kermicle 1969 *Science* 166:1422-1424).

Methods for obtaining haploid plants are also disclosed in Kobayashi, M. et al., *Journ. of Heredity* 71(1):9-14, 1980, Pollacsek, M., Agronomie (Paris) 12(3):247-251, 1992; Cho-Un-Haing et al., *Journ. of Plant Biol.*, 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, Maize Genet Coop. Newsletter 68:47; Chalyk, S. T., 1999, *Maize Genet. Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P. et al., 1988, *Theor. Appl. Genet.* 76:570-572 and 76:405-410; Tyrnov, V. S. et al., 1984, Dokl. Akad. Nauk. SSSR 276:735-738; Zabirova, E. R. et al., 1996, Kukuruza I Sorgo N4, 17-19; Aman, M. A., 1978, *Indian J. Genet Plant Breed* 38:452-457; Chalyk S. T., 1994, Euphytica 79:13-18; Chase, S. S., 1952, *Agron. J.* 44:263-267; Coe, E. H., 1959, *Am. Nat.* 93:381-382; Coe, E. H., and Sarkar, K. R., 1964 *J. Hered.* 55:231-233; Greenblatt, I. M. and Bock, M., 1967, *J. Hered.* 58:9-13; Kato, A., 1990, *Maize Genet. Coop. Newsletter* 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., Genetics and Molecular Biology, September 2000, 23(3):617-622; Tahir, M. S. et al. Pakistan Journal of Scientific and Industrial Research, August 2000, 43(4):258-261; Knox, R. E. et al. Plant Breeding, August 2000, 119(4):289-298; U.S. Pat. No. 5,639,951 and US Patent Publication No. 20020188965.

Thus, certain embodiments include a process for making a homozygous PH4DAZ progeny plant substantially similar to PH4DAZ by producing or obtaining a seed from the cross of PH4DAZ and another maize plant and applying double haploid methods to the F1 seed or F1 plant or to any successive filial generation. Such methods decrease the number of generations required to produce an inbred with similar genetics or characteristics to PH4DAZ. See Bernardo, R. and Kahler, A. L., Theor. Appl. Genet. 102:986-992, 2001.

In particular, a process of making seed substantially retaining the molecular marker profile of maize variety PH4DAZ is contemplated, such process comprising obtaining or producing F1 hybrid seed for which maize variety PH4DAZ is a parent, inducing double haploids to create progeny without the occurrence of meiotic segregation, obtaining the molecular marker profile of maize variety PH4DAZ, and selecting progeny that retain the molecular marker profile of PH4DAZ.

Another embodiment is a maize seed derived from inbred maize variety PH4DAZ produced by crossing a plant or plant part of inbred maize variety PH4DAZ with another plant, wherein representative seed of said inbred maize variety PH4DAZ has been deposited and wherein said maize seed derived from the inbred maize variety PH4DAZ has 92%, 93%, 94%, 95%, 96%, 97%, 98% or 99% of the same polymorphisms for molecular markers as the plant or plant part of inbred maize variety PH4DAZ. The number of molecular markers used for the molecular marker profile can be found in the Panzea database which is available online from Panzea. The type of molecular marker used in the molecular profile can be but is not limited to Single Nucleotide Polymorphisms, SNPs. A maize seed derived from inbred maize variety PH4DAZ produced by crossing a plant or plant part of inbred maize variety PH4DAZ with another plant, wherein representative seed of said inbred maize variety PH4DAZ has been deposited and wherein said maize seed derived from the inbred maize variety PH4DAZ has essentially the same morphological characteristics as maize variety PH4DAZ when grown in the same environmental conditions. The same environmental conditions may be, but is not limited to a side-by-side comparison. The characteristics can be those listed in Table 1. The comparison can be made using any number of professionally accepted experimental designs and statistical analysis.

Use of PH4DAZ in Tissue Culture

Methods of tissue culturing cells of PH4DAZ and a tissue culture of PH4DAZ is provided. As used herein, the term "tissue culture" includes plant protoplasts, plant cell tissue culture, cultured microspores, plant calli, plant clumps, and the like. In certain embodiments, the tissue culture comprises embryos, protoplasts, meristematic cells, pollen, leaves or anthers derived from immature tissues of pollen, flowers, kernels, ears, cobs, leaves, husks, stalks, roots, root tips, anthers, silk, and the like. As used herein, phrases such as "growing the seed" or "grown from the seed" include embryo rescue, isolation of cells from seed for use in tissue culture, as well as traditional growing methods.

Means for preparing and maintaining plant tissue cultures are well known in the art See, e.g., U.S. Pat. Nos. 5,538,880; 5,550,318, and 6,437,224, the latter describing tissue culture of maize, including tassel/anther culture. A tissue culture comprising organs such as tassels or anthers is provided which can be used to produce regenerated plants. (See, e.g., U.S. Pat. Nos. 5,445,961 and 5,322,789). Thus, in certain embodiments, cells are provided which upon growth and differentiation produce maize plants having the genotype and/or phenotypic characteristics of variety PH4DAZ.

Seed Treatments and Cleaning

Methods of harvesting the seed of the maize variety PH4DAZ as seed for planting are provided. Embodiments include cleaning the seed, treating the seed, and/or conditioning the seed. Cleaning the seed is understood in the art to include removal of foreign debris such as one or more of weed seed, chaff, and plant matter, from the seed. Conditioning the seed is understood in the art to include controlling the temperature and rate of dry down of the seed and storing seed in a controlled temperature environment. Seed treatment is the application of a composition to the seed such as a coating or powder. Methods for producing a treated seed include the step of applying a composition to the seed or seed surface. Seeds are provided which have on the surface a composition. Biological active components such as bacteria can also be used as a seed treatment. Some examples of compositions are insecticides, fungicides, pesticides, antimicrobials, germination inhibitors, germination promoters, cytokinins, and nutrients.

To protect and to enhance yield production and trait technologies, seed treatment options can provide additional crop plan flexibility and cost effective control against insects, weeds and diseases, thereby further enhancing the invention described herein. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematicides, avicides and/or molluscicides. These compounds are typically formulated together with further carriers, surfactants or application-promoting adjuvants customarily employed in the art of formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis*), *Bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, penicillium, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, trichoderma, trifloxystrobin, triticonazole and/or zinc. PCNB seed coat refers to EPA registration number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits in order to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

INDUSTRIAL APPLICABILITY

Another embodiment is a method of harvesting the grain or plant material of the F1 plant of variety PH4DAZ and using the grain or plant material in a commodity. Methods of producing a commodity plant product are also provided. Examples of maize grain or plant material as a commodity plant product include, but are not limited to, oils, meals, flour, starches, syrups, proteins, cellulose, silage, and sugars. Maize grain is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries. Processing the grain can include one or more of cleaning to remove foreign material and debris from the grain, conditioning, such as addition of moisture to the grain, steeping the grain, wet milling, dry milling and sifting.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Provided are plant parts other than the grain of maize and their use in industry: for example, methods for making stalks and husks into paper and wallboard and for using cobs for fuel and to make charcoal are provided.

The seed of maize variety PH4DAZ, the plant produced from the seed, the hybrid maize plant produced from the crossing of the variety, hybrid seed, and various parts of the hybrid maize plant and transgenic versions of the foregoing, can be utilized for human food, livestock feed, and as a raw material in industry.

All publications, patents, and patent applications mentioned in the specification are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications, and alterations may be applied to the compositions and/or methods described herein without departing from the true spirit, concept, and scope of the invention.

As used herein, the terms "comprises," "comprising," "includes," "including," "has," "having," "contains", "containing," "characterized by" or any other variation thereof, are intended to cover a non-exclusive inclusion.

Unless expressly stated to the contrary, "or" is used as an inclusive term. For example, a condition A or B is satisfied by any one of the following: A is true (or present) and B is false (or not present), A is false (or not present) and B is true (or present), and both A and B are true (or present). The indefinite articles "a" and "an" preceding an element or component are nonrestrictive regarding the number of instances (i.e., occurrences) of the element or component. Therefore "a" or "an" should be read to include one or at least one, and the singular word form of the element or component also includes the plural unless the number is obviously meant to be singular.

DEPOSITS

Applicant has made a deposit of at least 625 seeds of Maize Variety PH4DAZ with the Provasoli-Guillard National Center for Marine Algae and Microbiota (NCMA), 60 Bigelow Drive, East Boothbay, Me. 04544 USA, as NCMA Deposit No. 202204024. The seeds deposited with the NCMA on Apr. 8, 2022 were obtained from the seed of the variety maintained by Pioneer Hi-Bred International, Inc., 7250 NW $62^{nd}$ Avenue, Johnston, Iowa, 50131 since prior to the filing date of this application. Access to this seed will be available during the pendency of the application to the Commissioner of Patents and Trademarks and persons determined by the Commissioner to be entitled thereto upon request. Upon issuance of any claims in the application, the Applicant will make the deposit available to the public pursuant to 37 C.F.R. § 1.808. This deposit of the Maize Variety PH4DAZ will be maintained in the NCMA depository, which is a public depository, for a period of 30 years, or 5 years after the most recent request, or for the enforceable life of the patent, whichever is longer, and will be replaced if it becomes nonviable during that period. Additionally, Applicant has or will satisfy all of the requirements of 37 C.F.R. §§ 1.801-1.809, including providing an indication of the viability of the sample upon deposit. Applicant has no authority to waive any restrictions imposed by law on the transfer of biological material or its transportation in commerce. Applicant does not waive any infringement of rights granted under this patent or under the Plant Variety Protection Act (7 USC 2321 et seq.).

Breeding History of PH4DAZ

Inbred Maize variety PH4DAZ was developed by the following method. PH4DAZ is an elite corn inbred line originated from a cross between inbred line PH1MD0 and inbred line PH1DB1. The cross took place in Moorhead, Minn. in 2011. From this cross, ears were selected based on genetic analysis predicting disease, insect, and agronomic performance. Inbred PH4DAZ was developed by selfing the F1 plants, and selfing and using ear-to-row (pedigree) selection from the F2 to F7 generation, and bulking the F8 seed. Final developmental selections were made approximately the 6th generation in 2015 when the inred line was determined to be uniform and stable.

Maize variety PH4DAZ, being substantially homozygous, can be reproduced by planting seeds of the variety, growing the resulting maize plants under self-pollinating or sib-pollinating conditions with adequate isolation, and harvesting the resulting seed using techniques familiar to the agricultural arts.

TABLE 1

| VARIETY DESCRIPTION INFORMATION - PH4DAZ | | | |
|---|---|---|---|
| 1. | TYPE: | | |
| | Grain Texture | DENT | |
| 2. | MATURITY: | Days | Heat Units |
| | Comparative Relative Maturity (CRM) | 90 | |
| | Emergence to 50% of plants in silk | 48 | 1137 |
| | Emergence to 50% of plants in pollen shed | 48 | 1137 |
| 3. | PLANT: | Value | SE | Number |
| | Plant Height (to tassel tip) (cm) | 185.9 | 7.89 | 20 |
| | Ear Height (to base of top ear node) (cm) | 60.1 | 5.36 | 20 |
| | Length of Top Ear Internode (cm) | 11.4 | 0.96 | 20 |
| | Number of Nodes Above Ground | 12.5 | 0.8 | 20 |
| | Anthocyanin of Brace Roots: 1 = absent, 2 = faint, 3 = moderate, 4 = dark | 1 | | |
| 4. | LEAF: | | | |
| | Width of Ear Node Leaf (cm) | 8.8 | 0.54 | 20 |
| | Length of Ear Node Leaf (cm) | 76.4 | 5.11 | 20 |
| | Number of Leaves Above Top Ear | 4.8 | 0.4 | 20 |
| | Leaf Angle (Degrees) (at anthesis, 2nd leaf above top ear to stalk) | 31.5 | 3.57 | 20 |
| | Leaf Color | Med. Green | | |
| | Leaf Sheath Pubescence: 1 = none to 9 = peach-like fuzz | 1 | | |
| 5. | TASSEL: | | | |
| | Number of Primary Lateral Branches | 1.9 | 0.73 | 20 |
| | Number of Secondary Branches | 0 | 0 | 20 |
| | Branch Angle from Central Spike (Degrees) | 16 | 5.15 | 20 |
| | Tassel Length: (from peduncle node to tassel tip) (cm) | 56.4 | 3.58 | 20 |
| | Peduncle Length: (From top leaf node to lower branch) (cm) | 21.8 | 2.32 | 20 |
| | Central Spike Length (cm) | 30 | 2.8 | 20 |
| | Flag Leaf Length (cm) (from flag leaf collar to tassel tip) | 42.9 | 3.07 | 20 |
| | Pollen Shed: 0 = male sterile, 9 = heavy shed | 8 | | |
| | Bar Glumes (glume bands): 1 = absent, 2 = present | | | |
| | Anther Color: | Light Red | | |
| | Glume Color: | Med. Green | | |
| 6a. | EAR (Unhusked ear): | | | |
| | Silk color: (~3 days after silk emergence) | Med. Green | | |
| | Fresh husk color: | Light Green | | |
| | Dry husk color: (~65 days after 50% silking) | Buff | | |
| | Ear position at dry husk stage: (1 = upright, 2 = horizontal, 3 = pendant) | | | |
| | Husk Tightness: (1 = very loose, 9 = very tight) | 1 | | |
| | Husk Extension (at harvest): 1 = short (ears exposed), 2 = medium (<8 cm), 3 = long (8-10 cm), 4 = very long (>10 cm) | 2 | | |
| | Length of Interior Husk (cm) | 18.4 | 1.08 | 20 |
| 6b. | EAR (Husked ear data): | | | |
| | Shank Length (cm) | 11.3 | 2.23 | 20 |
| | Ear Length (cm) | 14.4 | 1.58 | 20 |
| | Ear Diameter at mid-point (mm) | 34.5 | 1.73 | 20 |
| | Ear Weight (gm) | 85 | 14.13 | 20 |
| | Number of Kernel Rows | 12.4 | 1.2 | 20 |
| | Number of Kernels Per Row | 26.1 | 3.6 | 20 |
| | Kernel Rows: 1 = indistinct, 2 = distinct | 2 | | |
| | Row Alignment: 1 = straight, 2 = slightly curved, 3 = spiral | 1 | | |
| | Ear Taper: 1 = slight cylind., 2 = average, 3 = extreme conic. | 1 | | |
| 7. | KERNEL (Dried): | | | |
| | Kernel Length (mm) | 10.3 | 0.36 | 20 |
| | Kernel Width (mm) | 8 | 0.45 | 20 |
| | Kernel Thickness (mm) | 4.4 | 0.46 | 20 |
| | Weight/100 Kernels (un-sized sample (gm) | 27.3 | | |
| | Kernel Pericarp color | 1 | | |
| | Aleurone Color Pattern | 1 | | |
| | Aleurone Color | Clear | | |
| | Hard Endosperm Color | Yellow | | |
| 8. | COB: | | | |
| | Cob Diameter at mid-point (mm) | 18.1 | 1.73 | 20 |
| | Cob Color | Red | | |

Number is the number of individual plants that were scored.
Value is an average if more than one plant or plot is scored.

What is claimed is:

1. A seed, plant, plant part, or plant cell of inbred maize variety PH4DAZ, representative seed of the variety having been deposited under NCMA accession number 202204024.

2. The plant part of claim 1, wherein the plant part is an ovule or pollen.

3. An F1 hybrid maize seed produced by crossing the plant or plant part of claim 1 with a different maize plant.

4. An F1 hybrid maize plant or plant part produced by growing the maize seed of claim 3, wherein the plant part comprises at least one cell of the F1 hybrid maize plant.

5. A method for producing a second maize plant, the method comprising applying plant breeding techniques to the F1 plant or plant part of claim 4 to produce the second maize plant.

6. A method for producing a second maize plant or plant part, the method comprising doubling haploid seed generated from a cross of the plant or plant part of claim 4 with an inducer variety, thereby producing the second maize plant or plant part.

7. A method of making a commodity plant product comprising silage, starch, fat, syrup or protein, the method comprising producing the commodity plant product from the maize plant or plant part of claim 4.

8. A method of producing a maize seed derived from the variety PH4DAZ, comprising:
   a) crossing the plant of claim 1 with itself or a second plant to produce progeny seed; and
   b) growing the progeny seed to produce a progeny plant and crossing the progeny plant with itself or a different plant to produce maize seed derived from the variety PH4DAZ.

9. A method for producing nucleic acids, the method comprising isolating nucleic acids from the seed, plant, plant part, or plant cell of claim 1.

10. A converted seed, plant, plant part or plant cell of inbred maize variety PH4DAZ, representative seed of the maize variety PH4DAZ having been deposited under NCMA accession number 202204024, wherein the converted seed, plant, plant part or plant cell comprises a locus conversion, and wherein the plant or a plant grown from the converted seed, plant part or plant cell comprises the locus conversion and otherwise comprises the physiological and morphological characteristics of maize variety PH4DAZ when grown under the same environmental conditions.

11. The converted seed, plant, plant part or plant cell of claim 10, wherein the locus conversion confers a property selected from the group consisting of male sterility, site-specific recombination, abiotic stress tolerance, altered phosphate, altered antioxidants, altered fatty acids, altered essential amino acids, altered carbohydrates, herbicide tolerance, insect resistance and disease resistance.

12. A maize seed produced by crossing the plant or plant part of claim 10 with a different maize plant.

13. A hybrid maize plant or plant part produced by growing the seed of claim 12, wherein the plant part comprises at least one cell of the hybrid maize plant.

14. A method for producing a second maize plant, the method comprising applying plant breeding techniques to the plant or plant part of claim 13 to produce the second maize plant.

15. A method for producing a second maize plant or plant part, the method comprising doubling haploid seed generated from a cross of the plant or plant part of claim 13 with an inducer variety, thereby producing the second maize plant or plant part.

16. A method of making a commodity plant product comprising silage, starch, fat, syrup or protein, the method comprising producing the commodity plant product from the maize plant or plant part of claim 13.

17. A method for producing nucleic acids, the method comprising isolating nucleic acids from the seed, plant, plant part, or plant cell of claim 10.

18. An F1 hybrid seed produced by crossing a plant or plant part of inbred maize variety PH4DAZ, representative seed of the variety having been deposited under NCMA accession number 202204024 with a different maize plant, wherein inbred maize variety PH4DAZ further comprises a transgene that is inherited by the seed, wherein the transgene was introduced into inbred maize variety PH4DAZ by backcrossing or genetic transformation.

19. A method of producing progeny seed, the method comprising crossing a plant grown from the seed of claim 18 with itself or a second plant to produce progeny seed.

20. A method of making a commodity plant product comprising silage, starch, fat, syrup or protein, the method comprising producing the commodity plant product from the maize plant or plant part of claim 18.

* * * * *